United States Patent
Baccelli et al.

(10) Patent No.: US 10,426,537 B2
(45) Date of Patent: Oct. 1, 2019

(54) METHOD AND INSTRUMENT FOR TENSIONING A FLEXIBLE TIE

(71) Applicant: Zimmer Spine S.A.S., Bordeaux (FR)

(72) Inventors: Christian Baccelli, Saucats (FR); Regis Le Couedic, Andresy (FR); Keyvan Mazda, Paris (FR)

(73) Assignee: Zimmer Spine, S.A.S., Bordeaux (FR)

( * ) Notice: Subject to any disclaimer, the term of this patent is extended or adjusted under 35 U.S.C. 154(b) by 0 days.

(21) Appl. No.: 15/921,418

(22) Filed: Mar. 14, 2018

(65) Prior Publication Data

US 2018/0199973 A1     Jul. 19, 2018

Related U.S. Application Data

(63) Continuation of application No. 13/154,257, filed on Jun. 6, 2011, now Pat. No. 9,949,778, which is a
(Continued)

(30) Foreign Application Priority Data

Sep. 21, 2005    (FR) ........................... 05 09629

(51) Int. Cl.
*A61B 17/88*     (2006.01)
*A61B 17/70*     (2006.01)
*A61B 17/84*     (2006.01)

(52) U.S. Cl.
CPC ...... *A61B 17/8861* (2013.01); *A61B 17/8869* (2013.01); *A61B 17/7053* (2013.01); *A61B 17/7062* (2013.01); *A61B 17/842* (2013.01)

(58) Field of Classification Search
CPC . A61B 17/88; A61B 17/8861; A61B 17/8869; A61B 17/7053; A61B 17/7062; A61B 17/842
(Continued)

(56) References Cited

U.S. PATENT DOCUMENTS

| 902,040 A | 10/1908 | Wyckoff et al. |
|---|---|---|
| 1,346,940 A | 7/1920 | Collins |

(Continued)

FOREIGN PATENT DOCUMENTS

| DE | 19716504 A1 | 12/1998 |
|---|---|---|
| EP | 0780096 A1 | 6/1997 |

(Continued)

OTHER PUBLICATIONS

"U.S. Appl. No. 11/996,918, Examiner Interview Summary dated Apr. 11, 2011", 3 pgs.
(Continued)

*Primary Examiner* — Juliana N Harvey
*Assistant Examiner* — Christina Negrellirodriguez
(74) *Attorney, Agent, or Firm* — Schwegman Lundberg & Woessner, P.A.

(57) ABSTRACT

A method and instrument for tensioning a flexible tie used for fastening an implant on a bony element by forming a first loop around it. In some embodiments, the instrument comprises a shaft having a distal end configured for contact with a rod, a moving part slidably engaged with the shaft, a holder connected to the moving part and configured to hold an end of the flexible tie, and a tension control member comprising a trigger that pivots relative to the moving part. In some embodiments, the method comprises coupling the end of the flexible tie to the instrument and squeezing the trigger to shorten the first loop of the flexible tie around the bony element, causing the moving part and the holder holding the end of the flexible tie to move in translation away from the distal end of the shaft, thereby exerting tension on the flexible tie.

19 Claims, 3 Drawing Sheets

Related U.S. Application Data continuation of application No. 12/408,592, filed on Mar. 20, 2009, now Pat. No. 8,323,318, which is a continuation of application No. 11/996,918, filed as application No. PCT/FR2006/050909 on Sep. 20, 2006, now Pat. No. 8,162,946.

(58) Field of Classification Search
USPC .................. 606/246, 263, 99, 103, 86 A
See application file for complete search history.

(56) References Cited

U.S. PATENT DOCUMENTS

| | | | |
|---|---|---|---|
| 2,049,361 A | 7/1936 | Johan | |
| 3,834,395 A | 9/1974 | Santos | |
| 4,570,618 A | 2/1986 | Wu | |
| 5,030,220 A | 7/1991 | Howland | |
| 5,304,178 A | 4/1994 | Stahurski | |
| 5,356,412 A | 10/1994 | Golds et al. | |
| 5,413,576 A | 5/1995 | Rivard | |
| 5,449,361 A | 9/1995 | Preissman | |
| 5,480,406 A | 1/1996 | Nolan et al. | |
| 5,496,318 A | 3/1996 | Howland et al. | |
| 5,609,634 A | 3/1997 | Voydeville | |
| 5,662,653 A | 9/1997 | Songer et al. | |
| 5,667,508 A | 9/1997 | Errico et al. | |
| 5,669,917 A | 9/1997 | Sauer et al. | |
| 5,693,061 A | 12/1997 | Pierce et al. | |
| 5,702,399 A | 12/1997 | Kilpeia et al. | |
| 5,720,751 A | 2/1998 | Jackson | |
| 5,772,663 A | 6/1998 | Whiteside et al. | |
| 5,782,831 A | 7/1998 | Sherman et al. | |
| RE36,221 E | 6/1999 | Breard et al. | |
| 5,935,133 A * | 8/1999 | Wagner | A61B 17/82 |
| | | | 606/103 |
| 5,938,663 A | 8/1999 | Petreto | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,179,838 B1 | 1/2001 | Fiz | |
| 6,200,318 B1 * | 3/2001 | Har-Shai | A61B 17/823 |
| | | | 140/123.6 |
| 6,228,096 B1 | 5/2001 | Marchand | |
| 6,241,740 B1 | 6/2001 | Davis et al. | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,325,802 B1 | 12/2001 | Frigg | |
| 6,352,557 B1 | 3/2002 | Ferree | |
| 6,391,030 B1 | 5/2002 | Wagner et al. | |
| 6,419,702 B1 | 7/2002 | Ferree | |
| 6,443,955 B1 | 9/2002 | Ahrend et al. | |
| 6,447,518 B1 | 9/2002 | Krause et al. | |
| 6,478,798 B1 | 11/2002 | Howland | |
| 6,514,255 B1 | 2/2003 | Ferree | |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | Deguillebon et al. | |
| 6,605,091 B1 | 8/2003 | Iwanski | |
| 6,616,669 B2 | 9/2003 | Ogilvie et al. | |
| 6,656,178 B1 | 12/2003 | Veldhuizen et al. | |
| 6,656,179 B1 | 12/2003 | Schaefer et al. | |
| 6,656,185 B2 | 12/2003 | Gleason et al. | |
| 6,682,533 B1 | 1/2004 | Dinsdale et al. | |
| 6,689,140 B2 | 2/2004 | Cohen | |
| 6,695,852 B2 | 2/2004 | Gleason | |
| 6,723,335 B1 | 4/2004 | Moehlenbruck et al. | |
| 6,746,452 B2 | 6/2004 | Tuke et al. | |
| 6,773,438 B1 | 8/2004 | Knodel | |
| 6,946,000 B2 | 9/2005 | Senegas et al. | |
| 7,481,828 B2 | 1/2009 | Mazda et al. | |
| 7,699,874 B2 | 4/2010 | Young | |
| 7,753,912 B2 | 7/2010 | Raymond et al. | |
| 7,909,853 B2 | 3/2011 | Zucherman et al. | |
| 7,959,554 B2 | 6/2011 | Mcalexander et al. | |
| 7,959,654 B2 | 6/2011 | Mazda et al. | |
| 8,162,946 B2 | 4/2012 | Baccelli et al. | |
| 8,323,318 B2 | 12/2012 | Baccelli et al. | |
| 8,814,910 B2 | 8/2014 | Baccelli et al. | |
| 9,949,778 B2 | 4/2018 | Baccelli et al. | |
| 2001/0034522 A1 | 10/2001 | Frigg | |
| 2002/0082600 A1 | 6/2002 | Shaolian et al. | |
| 2002/0116013 A1 | 8/2002 | Gleason et al. | |
| 2002/0198538 A1 | 12/2002 | Kortenbach et al. | |
| 2003/0004511 A1 | 1/2003 | Ferree | |
| 2003/0195628 A1 | 10/2003 | Bao et al. | |
| 2004/0087979 A1 | 5/2004 | Field et al. | |
| 2004/0097942 A1 | 5/2004 | Allen et al. | |
| 2004/0138666 A1 | 7/2004 | Fred, IV et al. | |
| 2005/0070958 A1 | 3/2005 | Swayze et al. | |
| 2005/0085815 A1 | 4/2005 | Harms et al. | |
| 2005/0131404 A1 | 6/2005 | Mazda et al. | |
| 2005/0154403 A1 | 7/2005 | Sauer et al. | |
| 2005/0177156 A1 | 8/2005 | Timm et al. | |
| 2005/0228375 A1 | 10/2005 | Mazda et al. | |
| 2005/0267420 A1 | 12/2005 | Young | |
| 2005/0273983 A1 | 12/2005 | Mattchen | |
| 2005/0283170 A1 | 12/2005 | Battles et al. | |
| 2006/0084988 A1 | 4/2006 | Kim | |
| 2006/0235387 A1 | 10/2006 | Peterman | |
| 2006/0235391 A1 | 11/2006 | Sutterlin, III | |
| 2007/0016190 A1 | 1/2007 | Martinez et al. | |
| 2007/0088359 A1 | 4/2007 | Woods et al. | |
| 2007/0299445 A1 | 12/2007 | Shadduck et al. | |
| 2008/0033557 A1 | 2/2008 | Pasquet et al. | |
| 2008/0058812 A1 | 3/2008 | Zehnder | |
| 2008/0125780 A1 | 5/2008 | Ferree | |
| 2008/0140133 A1 | 6/2008 | Allard et al. | |
| 2008/0208256 A1 | 8/2008 | Thramann | |
| 2009/0131985 A1 | 5/2009 | Mazda et al. | |
| 2009/0138048 A1 | 5/2009 | Baccelli et al. | |
| 2009/0326585 A1 | 12/2009 | Baccelli et al. | |
| 2011/0034956 A1 | 2/2011 | Mazda et al. | |
| 2011/0238118 A1 | 9/2011 | Baccelli et al. | |
| 2012/0022591 A1 | 1/2012 | Baccelli et al. | |

FOREIGN PATENT DOCUMENTS

| | | |
|---|---|---|
| EP | 1815812 A1 | 8/2007 |
| EP | 1933743 | 3/2011 |
| FR | 522040 A | 7/1921 |
| FR | 26156 E | 9/1923 |
| FR | 2704745 A1 | 11/1994 |
| FR | 2722088 A1 | 1/1996 |
| FR | 2799948 A1 | 4/2001 |
| FR | 2817929 A1 | 6/2002 |
| FR | 2867057 A1 | 9/2005 |
| FR | 2870718 A1 | 12/2005 |
| FR | 2890850 A1 | 3/2007 |
| FR | 2890851 A1 | 3/2007 |
| FR | 2897771 A1 | 8/2007 |
| GB | 2269753 A | 2/1994 |
| JP | 2001299770 A | 10/2001 |
| WO | WO-9416635 A1 | 8/1994 |
| WO | WO-199416635 A1 | 8/1994 |
| WO | WO-0154599 A1 | 8/2001 |
| WO | WO-0207621 A1 | 1/2002 |
| WO | WO-0207622 A1 | 1/2002 |
| WO | WO-0209604 A1 | 2/2002 |
| WO | WO-0217803 A2 | 3/2002 |
| WO | WO-02051326 A1 | 7/2002 |
| WO | WO-02071960 A1 | 9/2002 |
| WO | WO-03007829 A1 | 1/2003 |
| WO | WO-03103519 A2 | 12/2003 |
| WO | WO-2004010881 A1 | 2/2004 |
| WO | WO-2005020860 A3 | 3/2005 |
| WO | WO-2005120277 A1 | 12/2005 |
| WO | WO-2006034423 A2 | 3/2006 |
| WO | WO-2006106246 A2 | 10/2006 |
| WO | WO-2006106268 A2 | 10/2006 |
| WO | WO-2006106268 A3 | 10/2006 |

(56) References Cited

FOREIGN PATENT DOCUMENTS

| WO | WO-2007023240 | A2 | 3/2007 |
| WO | WO-2007023240 | A3 | 3/2007 |
| WO | WO-2007034112 | A1 | 3/2007 |
| WO | WO-200736657 | A1 | 4/2007 |
| WO | WO-2007036657 | A1 | 4/2007 |
| WO | WO-2007099258 | A2 | 9/2007 |
| WO | WO-2009130276 | A1 | 10/2009 |
| WO | WO-2009141393 | A1 | 11/2009 |

OTHER PUBLICATIONS

"U.S. Appl. No. 11/996,918, Preliminary Amendment filed Jan. 25, 2008", 8 pgs.
"U.S. Appl. No. 11/996,918, Response filed May 13, 2011 to Non Final Office Action dated Feb. 14, 2011", 11 pgs.
"U.S. Appl. No. 11/996,918, Response filed Nov. 17, 2011 to Final Office Action dated Aug. 17, 2011", 11 pgs.
"U.S. Appl. No. 12/408,592, Final Office Action dated Jan. 24, 2012", 18 pgs.
"U.S. Appl. No. 12/408,592, Notice of Allowance dated Sep. 27, 2012", 9 pgs.
"U.S. Appl. No. 12/408,592, Notice of Allowance dated Oct. 19, 2012", 3 pgs.
"U.S. Appl. No. 12/408,592, Preliminary Amendment filed Mar. 20, 2009", 2 pgs.
"U.S. Appl. No. 12/408,592, Response filed Apr. 24, 2012 to Final Office Action dated Jan. 24, 2012", 14 pgs.
"U.S. Appl. No. 12/408,592, Response filed Jun. 17, 2011 to Non Final Office Action dated Feb. 18, 2011", 14 pgs.
"U.S. Appl. No. 12/408,592, Response filed Dec. 21, 2011 to Non Final Office Action dated Sep. 22, 2011", 12 pgs.
"U.S. Appl. No. 13/154,983, Advisory Action dated Aug. 29, 2013", 3 pgs.
"U.S. Appl. No. 13/154,983, Corrected Notice of Allowance dated Jul. 30, 2014", 4 pgs.
"U.S. Appl. No. 13/154,983, Final Office Action dated Feb. 27, 2014", 8 pgs.
"U.S. Appl. No. 13/154,983, Final Office Action dated Jun. 14, 2013", 11 pgs.
"U.S. Appl. No. 13/154,983, Final Office Action dated Dec. 31, 2012", 14 pgs.
"U.S. Appl. No. 13/154,983, Non Final Office Action dated Jul. 3, 2012", 12 pgs.
"U.S. Appl. No. 13/154,983, Non Final Office Action dated Oct. 22, 2013", 9 pgs.
"U.S. Appl. No. 13/154,983, Notice of Allowance dated Apr. 3, 2014", 5 pgs.
"U.S. Appl. No. 13/154,983, Response filed Jan. 3, 2014 to Non Final Office Action dated Oct. 22, 2013", 10 pgs.
"U.S. Appl. No. 13/154,983, Response filed Feb. 28, 2013 to Final Office Action dated Dec. 31, 2012", 15 pgs.
"U.S. Appl. No. 13/154,983, Response filed Mar. 17, 2014 to Final Office Action dated Feb. 27, 2014", 8 pgs.
"U.S. Appl. No. 13/154,983, Response filed Mar. 30, 2012 to Restriction Requirement dated Mar. 1, 2012", 6 pgs.
"U.S. Appl. No. 13/154,983, Response filed Aug. 13, 2013 to Final Office Action dated Jun. 14, 2013", 12 pgs.
"U.S. Appl. No. 13/154,983, Response filed Oct. 2, 2012 to Non Final Office Action dated Jul. 3, 2012", 10 pgs.
"U.S. Appl. No. 13/154,983, Restriction Requirement dated Mar. 1, 2012", 6 pgs.
"European Application Serial No. 06831198.4, Decision to grant dated Feb. 24, 2011", 2 pgs.
"French Application Serial No. 200302307, International Search Report dated Jan. 2, 2004", 2 pgs.
"International Application Serial No. PCT/EP2008/064344, Written Opinion dated May 19, 2009", 7 pgs.
"Korean Application Serial No. 10-2005-7001238, Examination Report dated Feb. 23, 2010", 3 pgs.

"U.S. Appl. No. 10/521,914, Final Office Action dated Jul. 30, 2007", 13 pgs.
"U.S. Appl. No. 10/521,914, Non Final Office Action dated Mar. 19, 2008", 7 pgs.
"U.S. Appl. No. 10/521,914, Non Final Office Action dated Jun. 16, 2006", 12 pgs.
"U.S. Appl. No. 10/521,914, Non Final Office Action dated Dec. 29, 2006", 21 pgs.
"U.S. Appl. No. 11/877,160, Non Final Office Action dated Apr. 12, 2011", 11 pgs.
"U.S. Appl. No. 11/877,160, Non Final Office Action dated Nov. 26, 2010", 10 pgs.
"U.S. Appl. No. 11/877,160, Notice of Allowance dated Oct. 31, 2011", 8 pgs.
"U.S. Appl. No. 11/996,918, Final Office Action dated Aug. 17, 2011", 11 pgs.
"U.S. Appl. No. 11/996,918, Non Final Office Action dated Feb. 14, 2011", 12 pgs.
"U.S. Appl. No. 11/996,918, Notice of Allowance dated Dec. 19, 2011", 7 pgs.
"U.S. Appl. No. 12/059,634, Final Office Action dated Jun. 22, 2011", 15 pgs.
"U.S. Appl. No. 12/059,634, Non Final Office Action dated Feb. 15, 2011", 15 pgs.
"U.S. Appl. No. 12/059,634, Non Final Office Action dated Oct. 5, 2011", 12 pgs.
"U.S. Appl. No. 12/358,748, Non Final Office Action dated Sep. 15, 2010", 7 pgs.
"U.S. Appl. No. 12/358,748, Notice of Allowance dated Feb. 23, 2011", 5 pgs.
"U.S. Appl. No. 12/375,265, Notice of Allowance dated Aug. 25, 2011", 10 pgs.
"U.S. Appl. No. 12/408,592, Non Final Office Action dated Feb. 18, 2011", 17 pgs.
"U.S. Appl. No. 12/408,592, Non Final Office Action dated Sep. 22, 2011", 24 pgs.
"U.S. Appl. No. 13/154,257, Appeal Brief filed Feb. 20, 2015", 16 pgs.
"U.S. Appl. No. 13/154,257, Appeal Decision dated Jan. 22, 2015", 2 pgs.
"U.S. Appl. No. 13/154,257, Appeal Decision dated Oct. 3, 2017", 8 pgs.
"U.S. Appl. No. 13/154,257, Examiner's Answer dated Aug. 13, 2015", 16 pgs.
"U.S. Appl. No. 13/154,257, Final Office Action dated Sep. 24, 2012", 10 pgs.
"U.S. Appl. No. 13/154,257, Final Office Action dated Nov. 5, 2014", 18 pgs.
"U.S. Appl. No. 13/154,257, Non Final Office Action dated Feb 29, 2012", 14 pgs.
"U.S. Appl. No. 13/154,257, Non Final Office Action dated May 15, 2014", 16 pgs.
"U.S. Appl. No. 13/154,257, Non Final Office Action dated Nov. 5, 2013", 12 pgs.
"U.S. Appl. No. 13/154,257, Notice of Allowance dated Dec. 15, 2017", 5 pgs.
"U.S. Appl. No. 13/154,257, Pre-Appeal Brief Request filed Dec. 18, 2014", 6 pgs.
"U.S. Appl. No. 13/154,257, PTO Response to Rule 312 Communication dated Jan. 22, 2018", 2 pgs.
"U.S. Appl. No. 13/154,257, Response filed Feb. 5, 2014 to Non Final Office Action dated Nov. 5, 2013", 11 pgs.
"U.S. Appl. No. 13/154,257, Response filed May 25, 2012 to Non Final Office Action dated Feb. 29, 2012", 10 pgs.
"U.S. Appl. No. 13/154,257, Response filed Jul. 14, 2014 to Non Final Office Action dated May 15, 2014", 16 pgs.
"U.S. Appl. No. 13/154,257, Response filed Nov. 7, 2017 to Appeal Decision dated Oct. 3, 2017", 7 pgs.
"U.S. Appl. No. 13/154,257, Response filed Nov. 20, 2012 to Final Office Action dated Sep. 24, 2012", 11 pgs.
"U.S. Appl. No. 13/907,040, Final Office Action dated Sep. 24, 2012", 10 pgs.

(56) References Cited

OTHER PUBLICATIONS

"U.S. Appl. No. 14/559,121, Non Final Office Action dated Feb. 29, 2012", 14 pgs.

"U.S. Appl. No. 14/559,121, Non Final Office Action dated May 15, 2014", 16 pgs.

"U.S. Appl. No. 14/559,121, Non Final Office Action dated Nov. 5, 2013", 12 pgs.

"Australian Application Serial No. 2003267529, Search Report dated Nov. 15, 2007", 2 pgs.

"European Application Serial No. 07301454.0, Extended European Search Report dated Sep. 25, 2008", 8 pgs.

"European Application Serial No. 07301483.9, Extended European Search Report dated Jul. 10, 2008", 10 pgs.

"European Application Serial No. 07301483.9, Partial European Search Report dated Apr. 23, 2008", 6 pgs.

"European Application Serial No. 08305124.3, Extended European Search Report dated Oct. 24, 2008", 4 pgs.

"European Application Serial No. 08305183, European Search Report dated Mar. 19, 2009", 10 pgs.

"European Application Serial No. 08305326, European Search Report dated Nov. 12, 2008", 2 pgs.

"European Application Serial No. 08305326, European Search Report dated Nov. 25, 2008", 3 pgs.

"European Application Serial No. 20070301483, European Search Report dated Apr. 15, 2008", 10 pgs.

"French Application Serial No. 0209317, Preliminary Search Report dated Apr. 9, 2003", 2 pgs.

"French Application Serial No. 0405611, Preliminary Search Report dated Jan. 12, 2005", 2 pgs.

"French Application Serial No. 0509570, Preliminary Search Report dated Jun. 29, 2006", 2 pgs.

"French Application Serial No. 0509629, Preliminary Search Report dated Jun. 9, 2006", 2 pgs.

"French Application Serial No. 0757814, Preliminary Search Report dated May 22, 2008", 2 pgs.

"French Application Serial No. 200650609, Preliminary Search Report and Written Opinion dated Jun. 30, 2006", 5 pgs.

"International Application Serial No. PCT/EP2008/062791, International Search Report dated Dec. 4, 2008", 3 pgs.

"International Application Serial No. PCT/EP2008/062791, Written Opinion dated Dec. 4, 2008", 6 pgs.

"International Application Serial No. PCT/EP2008/063682, International Preliminary Report on Patentability dated Apr. 13, 2010", 8 pgs.

"International Application Serial No. PCT/EP2008/063682, International Search Report dated Nov. 24, 2008", 3 pgs.

"International Application Serial No. PCT/EP2008/063682, Written Opinion dated Nov. 24, 2008", 7 pgs.

"International Application Serial No. PCT/EP2008/064344, International Preliminary Report on Patentability dated Apr. 27, 2010", 8 pgs.

"International Application Serial No. PCT/EP2008/064344, International Search Report dated May 19, 2009", 4 pgs.

"International Application Serial No. PCT/FR2003/002307, International Search Report dated Jan. 2, 2004", 2 pgs.

"International Application Serial No. PCT/FR2005/001280, Written Opinion dated Nov. 7, 2005", 5 pgs.

"International Application Serial No. PCT/FR2006/050898, International Preliminary Report on Patentability dated Apr. 29, 2008", 6 pgs.

"International Application Serial No. PCT/FR2006/050898, International Search Report dated Feb. 2, 2007", 2 pgs.

"International Application Serial No. PCT/FR2006/050898, Written Opinion dated Apr. 28, 2008", 5 pgs.

"International Application Serial No. PCT/FR2006/050909, International Preliminary Report on Patentability dated Apr. 8, 2008", 11 pgs.

"International Application Serial No. PCT/FR2006/050909, International Search Report dated Jan. 24, 2007", 6 pgs.

"International Application Serial No. PCT/FR2006/050909, Written Opinion dated Jan. 24, 2007", 9 pgs.

"International Application Serial No. PCT/FR2006/050909, Written Opinion dated Apr. 2, 2008", 4 pgs.

"International Application Serial No. PCT/US2009/038977, International Preliminary Report on Patentability dated May 27, 2010", 6 pgs.

"International Application Serial No. PCT/US2009/038977, International Search Report dated Jul. 22, 2009", 4 pgs.

"International Application Serial No. PCT/US2009/038977, Written Opinion dated Feb. 24, 2010", 7 pgs.

"International Application Serial No. PCT/US2009/038977, Written Opinion dated Jul. 22, 2009", 8 pgs.

"International Application Serial No. PCT/EP2008/062791, International Preliminary Report on Patentability dated Mar. 30, 2010", 7 pgs.

"International Application Serial No. PCT/FR2005/001280, International Search Report dated Nov. 7, 2005", 6 pgs.

* cited by examiner

METHOD AND INSTRUMENT FOR TENSIONING A FLEXIBLE TIE

CROSS-REFERENCE TO RELATED APPLICATIONS

This application is a continuation of and claims a benefit of priority under 35 U.S.C. § 120 from U.S. patent application Ser. No. 12/408,592, filed Mar. 20, 2009, entitled "FLEXIBLE TIE FASTENING SYSTEM," which is a continuation of and claims priority from U.S. patent application Ser. No. 11/996,918, filed Jan. 25, 2008, entitled "AN INSTRUMENT FOR TENSIONING A FLEXIBLE TIE," which is the National Stage of International Application No. PCT/FR2006/050909, filed Sep. 20, 2006, which claims priority from French Patent Application No. 0509629, filed on Sep. 21, 2005. This application also relates to U.S. patent application Ser. No. 13/154,257, filed Jun. 6, 2011, entitled "SPINAL IMPLANT WITH FLEXIBLE TIE." The content of each application referenced herein is hereby incorporated as if fully set forth herein.

TECHNICAL FIELD OF THE INVENTION

The invention relates to a method and instrument for tensioning a flexible tie used for fastening an implant on a bony element by forming a first loop around the bony element.

BACKGROUND OF THE RELATED ART

The spine is made up of a superposition of vertebrae, that are normally aligned along a vertebral axis, going from the lumbar vertebrae to the cervical vertebrae, with each vertebra presenting a posterior wall from which there projects a spinous process and two side edges having walls from which there project the ribs and/or transverse processes. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve.

In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

SUMMARY OF THE INVENTION

The hooks are generally inserted in pairs in each vertebra and on either side close to the pedicles, the heads of the hooks projecting from the posterior wall of a vertebra, one on either side of the spinous process. The heads may be tulip-shaped, for example, and they are suitable for receiving a rod which is secured by means of a nut screwed onto the head and bearing against the rod. Rows constituted by the heads of the hooks situated on either side of the spinous processes are interconnected and held in fixed position by two rods that are parallel to each other and to the axis of the spine.

Nevertheless, using such hooks is tricky, since under no circumstances must the operator harm the spinal cord that extends in the center of the spinal canal, since that would lead to paralysis for the patient.

The use of screws makes it possible to reduce the risks of such surgery. They likewise have tulip-shaped heads and they are inserted in pairs in the posterior walls of vertebrae in the pedicles on either side of the spinous processes. Thus, the screws constitute fastening points in the vertebrae for holding them relative to one another. Nevertheless, the screws are necessarily inserted into the pedicles of the vertebrae, and under certain circumstances, the pedicles may be small in size or they may be damaged.

A problem which arises, and which the invention seeks to solve, is how to obtain such fastening points when it is not possible to introduce screws into the vertebrae in the curved portion, and when using hooks would be too dangerous.

In PCT patent application WO 2004/010881 in the name of the Applicant, a vertebral fastener system is described that enables this problem to be solved.

That vertebral fastener system suitable for mounting on a vertebra of the spine for connection to a rod comprises:
a connection piece disposed facing said rib and/or said transverse process, and suitable for being connected to said rod;
a flexible tie of elongate shape suitable for connecting together said connection piece and at least one rib and/or transverse process; and
adjustable locking means secured to said connection piece, said tie presenting a first end secured to said connection piece and a free second end suitable for sliding in said connection piece and to form a loop, said locking means being suitable for simultaneously holding said connection piece in a fixed position relative to the rod and a portion of said tie extending between said ends being suitable for being locked in translation relative to said connection piece by said adjustable locking means, whereby the loop presents a length that is determined in such a manner as to prevent relative displacement of said rod and of said vertebra in opposite directions.

Other flexible tie systems for fastening to a vertebra can be used. This applies in particular to the system shown in accompanying FIG. 1.

Figure 1:
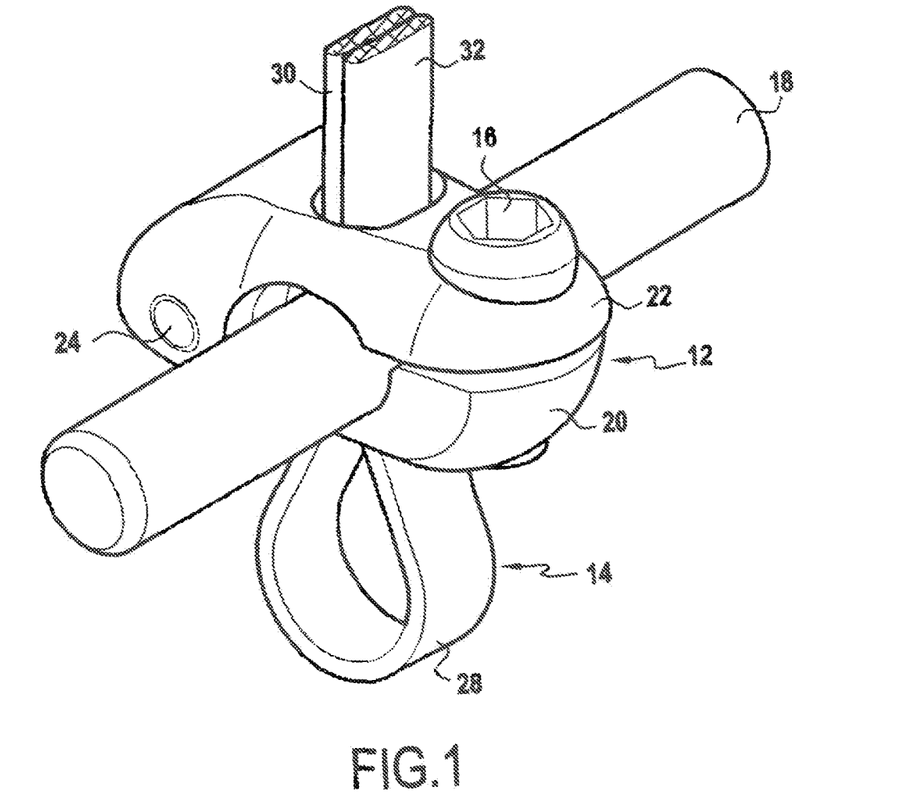
FIG. 1, described above, shows an example of an implant with a fastener tie with which the instrument of the invention can advantageously be used.

It comprises a connection piece 12 constituted by two jaws 20 and 22 that are hinged together at one end about an axis 24. The two jaws have recesses enabling a rod 18 to be put into place and allowing a braid or tie 14 to pass through, the tie forming a loop 28 on one side of the connection piece 12 and two free ends 30 and 32 on the other side of said piece. The connection system also has a locking member constituted by a screw 16 that can be engaged in the ends of the jaws 20 and 22 remote from their hinged ends. The portions of the tie 14 that are engaged in the recesses are secured to the connection piece by being pinched between the walls of the recesses in the connection piece and the rod 18 when the locking screw 16 is fully tightened.

It can be understood that in order to ensure that said assembly is properly fastened on a transverse process, on a rib, or on a portion of the posterior arc of a vertebra, it is necessary to exert tension on the free ends 30 and 32 of the tie 14.

It will also be understood that with the first-described fastener system, it is also necessary to exert tension on the single free end of the tie in order to ensure correct fastening on the bony element.

U.S. Pat. No. 5,964,769 discloses a device serving to exert tension on a cable used for fastening a medical device on a bone. That device presents the drawbacks of acting directly on the tie-tightening device and no disposition allows the tension exerted on the tie to be controlled.

An object of the invention is to provide an instrument for tensioning a flexible tie of an implant that ensures that it is tensioned effectively while nevertheless being easy for the surgeon to use.

To achieve this object, the invention provides an instrument for tensioning a flexible tie used for fastening an implant onto a bony element of a patient by forming a first loop around the bony element, said tie presenting at least one end that projects out from said implant, and said instrument comprises:

- a rod having a first end provided with bearing means for bearing against said implant;
- a moving part that is movable in translation and that surrounds said rod over a fraction of its length;
- holder means for holding the end of said tie, said holder means being connected to said moving part by a dynamometer system; and
- control means mounted on said moving part to cause the moving part to move relative to said rod, thereby tending to move the first end of the rod away from said moving part, thereby exerting tension on said tie relative to said implant.

It will be understood that since the rod bears against the implant, the moving part is secured either to the second loop of the tie, or to the free end of said tie serves to exert tension on said tie, thereby ensuring appropriate tightening of the first loop of the tie on the bony element.

In addition, when the surgeon acts on the control means, the surgeon knows when the appropriate tension has been applied, thus making it possible to avoid untimely breaking of the tie or damage to the bony element.

Preferably, the instrument further comprises an anti-return system for temporarily preventing said rod and said moving part moving in translation relative to each other, in the absence of action on the control means.

Preferably, the dynamometer system comprises a carriage that is movable in translation relative to the rod and to the moving part, said tie-holder stud being secured to said carriage, and a compression spring being interposed between said carriage and a portion of the moving part.

Also preferably, the control means comprise a trigger mounted to pivot relative to the moving part and presenting a manual actuator portion and a finger that acts on said rod.

Also preferably, the instrument further comprises a handle secured to said moving part and disposed in such a manner that the user can grasp said trigger and said handle simultaneously.

BRIEF DESCRIPTION OF THE DRAWINGS

Other characteristics and advantages of the invention appear better on reading the following description of an embodiment of the invention given by way of non-limiting example. The description refers to the accompanying figures, in which.

DETAILED DESCRIPTION

Figure 2:
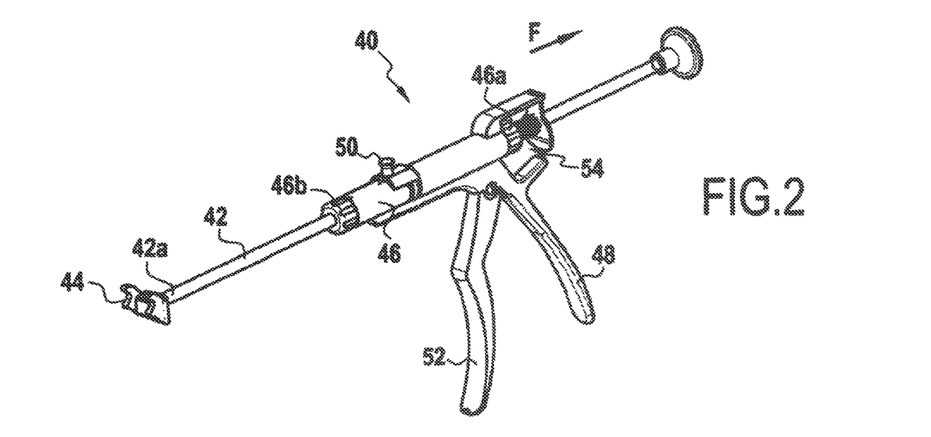
FIG. 2 is a perspective view of the instrument assembly of the invention.

With reference initially to FIG. 2, there follows a description of the instrument assembly 40. It is essentially constituted by a rod 42 having a first end 42a fitted with bearing means 44 for bearing against the implant on which the tie is to be tensioned. The instrument 40 also has a moving part 46 that is movable in translation relative to the rod 42. The moving part 46 is generally cylindrical in shape and is provided with a handle 48. The moving part 46 also has a stud 50 on its portion remote from the handle 48. As explained below, the stud 50 serves to hold the tie on which tension is to be applied. The instrument 40 also comprises a control member constituted by a trigger 52. As explained below, actuating the trigger 52 serves to cause the moving part 46 to move rearwards relative to the rod 42 in the direction of arrow F. In addition, at its end 46a opposite from its end 46b closest to the bearing element 44, the moving part 46 is fitted with an anti-return system acting on the rod 42. As explained in greater detail below, the anti-return system 54 enables the rod 42 and the moving part 46 to be held together temporarily in translation so long as no action is exerted on the trigger 52.

Figure 4:
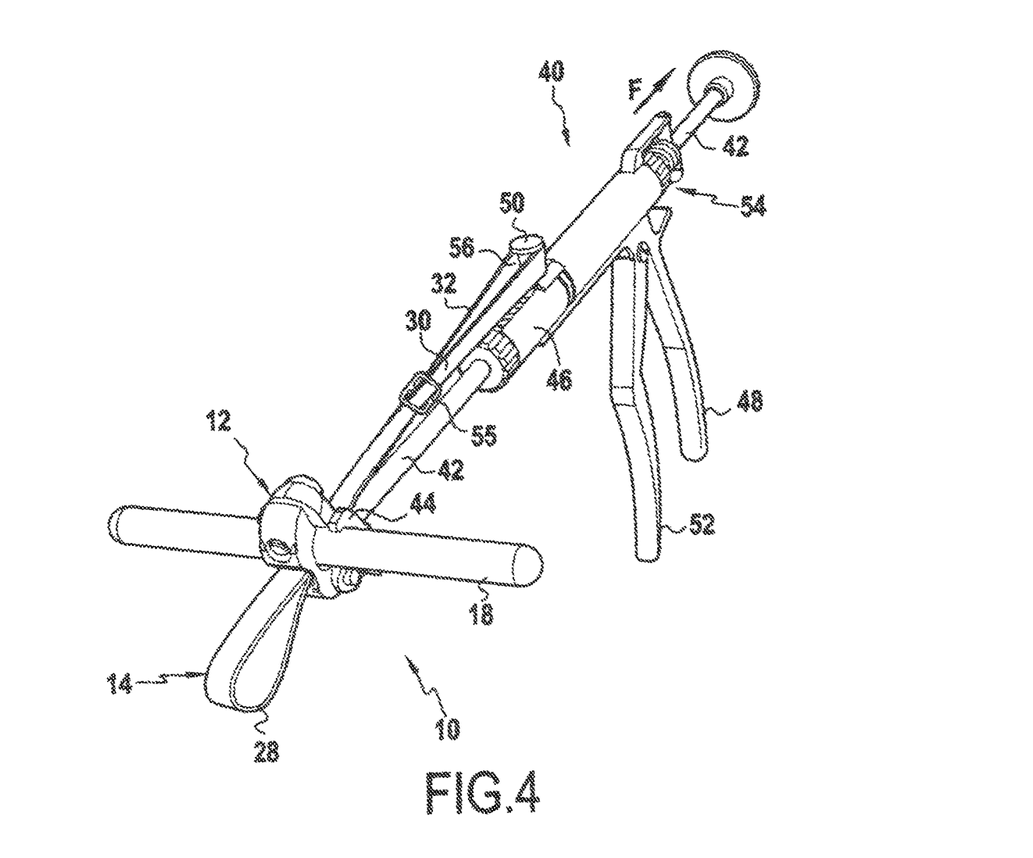
FIG. 4 is a perspective view showing the instrument in use with an implant of the type shown in FIG. 1.

With reference more particularly to FIG. 4, there follows a description in general terms of how the instrument 40 is used. In this figure, there can be seen a vertebral fastener system 10 of the type shown in FIG. 1. In this figure, there can be seen the rod 18, the connection piece 12, and the first fastener loop 28 formed by the tie 14 of the fastener system. This figure also shows that the free end 32 of the tie 14 is connected to the other free end 30 of the same tie by a fastener element 55 of suitable type. Thus, the tie 14 forms a second loop 56.

In use, the bearing means 44 of the instrument bear against the rod 18 on either side of the connection piece 12. The second loop 56 of the tie 14 is engaged on the stud 50 of the moving part 46 of the instrument. It will be understood that when the surgeon exerts action by using the trigger 52 and the handle 48, this causes the moving part 46 to move backwards in the direction F relative to the rod 18, thereby applying traction to the tie as a whole, and in particular to its loop 28. The surgeon can exert successive actions on the trigger 52 because of the presence of the anti-return system 54. As explained below, the instrument is preferably also fitted with a dynamometer system that enables the surgeon to see when a suitable tension has been exerted on the tie 14. Once the suitable tension has been exerted, the instrument 40 is separated from the loop 56 in the tie 14, and the portions of the tie 14 that project beyond the connection piece 12 are cut off.

Figure 3:
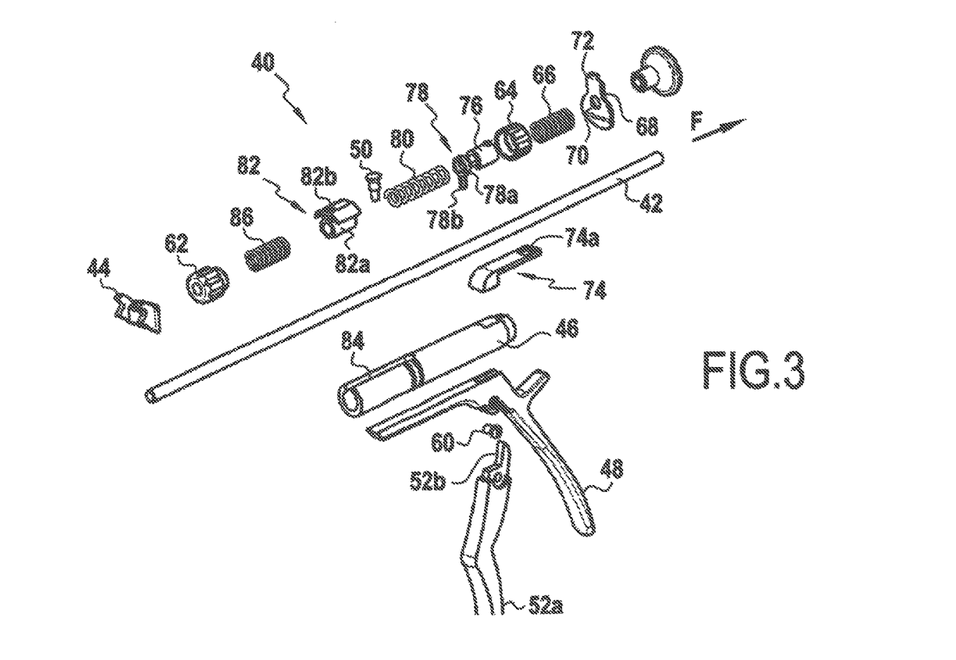
FIG. 3 is an exploded view of the disassembled instrument showing its internal mechanisms.

With reference to FIG. 3, there follows a description in greater detail of the mechanisms of the instrument 40. This figure shows the cylindrically-shaped moving part 46 on which the handle 48 is secured. The trigger 52 is hinged relative to the handle 48 about a pin 60. The trigger 52 has a grip portion 52a and a finger 52b for controlling the rod 42, for which finger 52b projects beyond the pivot pin 60. The finger 52b penetrates into the moving part 46 via a slot (not shown). The rod 42 is slidably engaged in the moving part 46.

Various elements that are described below are mounted around the rod 42 inside the moving part 46 having open ends that are closed by endpieces 62 and 64 each pierced by an axial bore for passing the rod 42. A spring 66 and a plate 68 constituting the anti-return system are mounted outside the moving part 46, around the rod 42. The plate 68 is pierced by a bore 70 of diameter that is slightly greater than the diameter of the rod. The plate 68 has a tongue 72 that can bear against an arm 74 secured to the rear portion of the moving part 46. Inside the moving part 46 and starting from its end closed by the endpiece 64, there is a spacer cylinder 76, a transmission part 78 constituted by an annular portion 78a and by a stud 78b suitable for co-operating with the finger 52b of the trigger 52. The transmission part 78 is associated with a spring 80. Thereafter there is a carriage 82 having a cylindrical portion 82a engaged around the rod 42 and two external projections 82b. The projections 82b of the carriage 82 are external to the moving part 46 by virtue of a longitudinal slot 84 therein. This external portion of the carriage 82 has the tie-holding stud 50 secured thereto. The carriage 82 is associated with a dynamometer spring 86 which is interposed between the endpiece 62 and the front face of the cylindrical portion 82a of the carriage 82.

In the absence of any action on the trigger 52, the plate 68 of the anti-return system slopes relative to the rod 42 because of the presence of the end 74a of the arm 74, thus causing the rod 42 and the moving part 46 to be temporarily secured to each other in translation. When action is exerted on the trigger 52, the movement of the rod releases the plate 68 and thus allows the rod 42 to move relative to the moving part 46. Similarly, when no action is applied to the trigger 52, the transmission part 78 is free, whereas, in contrast, when action is applied to the trigger 52, the finger 52b acts on the stud 78b of the transmission part 78, thereby temporarily securing it to the rod 42. This temporary connection serves to move the rod 42 relative to the part 46 under the effect of the trigger being actuated.

The dynamometer system operates in simple manner. Under the effect of the rod 42 moving in the direction F relative to the part 46, the dynamometer spring 86 is compressed, causing the carriage 82 to perform relative movement. A mark on the outside face of the moving part 46 makes it possible to detect when the appropriate tension has been applied, this tension corresponding naturally to the dynamometer spring 86 being subjected to predetermined compression.

In the description above, it is assumed that the tie 14 has a second loop used for holding onto the tensioning stud 50 of the instrument. When the tie of the implant has only one free end, this end can be held on the stud 50 or on any other appropriate fastener system so as to exert in the same manner the desired tension on the end of the tie and thus on the loop 28 formed thereby.

What is claimed is:

1. An instrument for tensioning a flexible tie, comprising:
    a shaft comprising a distal end configured for contact with a rod;
    a moving part slidably engaged with the shaft along an actuation axis;
    a holder connected to the moving part and configured to hold an end of the flexible tie, the holder being movable in translation relative to the shaft;
    a tension control member connected to the moving part and configured to cause the moving part and the holder holding the end of the flexible tie to move in translation away from the distal end of the shaft along the actuation axis, thereby exerting tension on the flexible tie;
    a handle extending from the moving part transverse to the actuation axis;
    a trigger that is pivotable relative to the moving part toward the handle to engage the tension control member and cause the moving part and the holder to move along the actuation axis;
    a dynamometer system located in the moving part and configured to provide a visual indication of a magnitude of tension in the flexible tie held by the holder as the trigger is actuated;
    a carriage disposed at least partially within the moving part, the holder extending from the carriage;
    a first spring located in the moving part adjacent the carriage and extending toward the distal end of the shaft;
    a second spring located in the moving part between the carriage and the tension control member; and
    a longitudinal slot located on the moving part, wherein the holder extends from the carriage through the longitudinal slot.

2. An instrument according to claim 1, wherein the flexible tie comprises a first loop configured to wrap around a bony element and wherein the end of the flexible tie held by the holder comprises a second loop of the flexible tie.

3. An instrument according to claim 2, wherein the holder comprises a capture post and wherein the second loop is wrapped around the capture post.

4. An instrument according to claim 3, wherein the dynamometer system comprises: a tension gauge located at a distal end of the capture post.

5. An instrument according to claim 4, wherein the tension gauge comprises an indicator line on an outer surface of the moving part.

6. An instrument according to claim 1, further comprising: an anti-return mechanism for temporarily preventing the moving part and the shaft moving in translation relative to each other in absence of any action on the trigger.

7. An instrument according to claim 1, wherein the handle is disposed in proximity to the trigger to allow for simultaneous grasping of both the handle and the trigger, wherein the trigger further comprises a finger extending into the moving part, and wherein rotating the trigger in a first direction relative to the handle engages the finger of the trigger with the shaft.

8. An instrument according to claim 7, wherein further rotation of the trigger in the first direction moves the moving part in translation away from the distal end of the shaft to tension the flexible tie, and wherein releasing the trigger disengages the finger from the shaft.

9. An instrument according to claim 7, further comprising:
    a plate comprising an opening through which the shaft is received, the opening of the plate comprising a diameter that is slightly greater than a diameter of the shaft;
    an arm extending from the moving part; and
    a spring, wherein when the trigger is disengaged from the shaft the arm biases the plate to a sloped orientation relative to the shaft to inhibit movement, and wherein when the trigger engages the shaft and moves the shaft in the first direction, the spring biases the plate into a substantially perpendicular orientation relative to the shaft to enable translational movement of the moving part relative to the shaft, the shaft being translatable through the opening of the plate.

10. An instrument according to claim 1, further comprising: a mark on an outer surface of the moving part adjacent the longitudinal slot, the mark indicating a level of tension applied onto the flexible tie.

11. An instrument according to claim 10, wherein the level of tension corresponds to the first spring being subjected to a predetermined amount of compression.

12. An instrument according to claim 1, further comprising an endpiece connected to the moving part at an end located toward the distal end of the shaft, wherein the first spring is located between the endpiece and the carriage.

13. An instrument according to claim 1, wherein tension in the first spring is independent of a location of the shaft relative to the moving part.

14. An instrument for tensioning a flexible tie, comprising:
- a rod extending along an axis, the rod comprising:
  - a first end configured to engage an implantable stiffening rod; and
  - a second end disposed opposite the first end;
- a body through which a length of the rod is configured to extend, the body comprising:
  - a first end located toward the first end of the rod;
  - a second end located toward the second end of the rod; and
  - a longitudinal slot;
- a carriage located at least partially within the body and comprising a bore through which the rod extends;
- a post extending from the carriage transverse to the axis, the post extending through the longitudinal slot;
- a first spring located in the body between the first end of the body and the carriage; and
- a mark located on the body to provide a visual indication of compression placed on the first spring between the first end of the body and the carriage regardless of a position of the rod relative to the body.

15. An instrument according to claim 14, wherein the compression placed on the first spring directly corresponds to tension placed on a flexible tie coupling the post and a connection piece.

16. An instrument according to claim 14, wherein the first spring is visible in the longitudinal slot and the mark is located adjacent the longitudinal slot.

17. An instrument according to claim 14, further comprising a
- a handle extending from the body; and
- a trigger pivotably coupled to the instrument relative to the handle, the trigger configured to advance the rod along the axis when actuated.

18. An instrument according to claim 17, further comprising:
- a second spring located in the body adjacent the carriage opposite the first spring; and
- a transmission part disposed in the body adjacent the second spring and configured to interact with the trigger.

19. An instrument for tensioning a flexible tie, comprising:
- a shaft comprising a distal end configured for contact with a rod;
- a moving part slidably engaged with the shaft along an actuation axis;
- a holder connected to the moving part and configured to hold an end of the flexible tie, the holder being movable in translation relative to the shaft;
- a tension control member connected to the moving part and configured to cause the moving part and the holder holding the end of the flexible tie to move in translation away from the distal end of the shaft along the actuation axis, thereby exerting tension on the flexible tie;
- a handle extending from the moving part transverse to the actuation axis;
- a trigger that is pivotable relative to the moving part toward the handle to engage the tension control member and cause the moving part and the holder to move along the actuation axis;
  - wherein the handle is disposed in proximity to the trigger to allow for simultaneous grasping of both the handle and the trigger, wherein the trigger further comprises a finger extending into the moving part, and wherein rotating the trigger in a first direction relative to the handle engages the finger of the trigger with the shaft;
- a dynamometer system located in the moving part and configured to provide a visual indication of a magnitude of tension in the flexible tie held by the holder as the trigger is actuated;
- a plate comprising an opening through which the shaft is received, the opening of the plate comprising a diameter that is slightly greater than a diameter of the shaft;
- an arm extending from the moving part; and
- a spring, wherein when the trigger is disengaged from the shaft the arm biases the plate to a sloped orientation relative to the shaft to inhibit movement, and wherein when the trigger engages the shaft and moves the shaft in the first direction, the spring biases the plate into a substantially perpendicular orientation relative to the shaft to enable translational movement of the moving part relative to the shaft, the shaft being translatable through the opening of the plate.

* * * * *